United States Patent [19]

Lamb

[11] 4,038,389

[45] July 26, 1977

[54] MEDROXYPROGESTERONE ACETATE COMPOSITIONS

[75] Inventor: Donald J. Lamb, Portage, Mich.

[73] Assignee: The Upjohn Company, Kalamazoo, Mich.

[21] Appl. No.: 671,918

[22] Filed: Mar. 29, 1976

Related U.S. Application Data

[63] Continuation-in-part of Ser. No. 587,747, May 7, 1975, abandoned, which is a continuation of Ser. No. 395,667, Sept. 10, 1973, abandoned, which is a continuation of Ser. No. 296,943, July 17, 1972, abandoned, which is a continuation of Ser. No. 74,163, Sept. 21, 1970, abandoned, which is a continuation-in-part of Ser. No. 714,436, March 20, 1968, abandoned, which is a continuation of Ser. No. 387,230, Aug. 3, 1964, abandoned.

[51] Int. Cl.$^2$ .............................................. A61K 31/56
[52] U.S. Cl. .................................................... 424/243
[58] Field of Search ................................ 424/238, 243

[56] References Cited

U.S. PATENT DOCUMENTS

| 3,008,875 | 11/1961 | Dale ......................................... 424/81 |
| 3,147,290 | 9/1964 | Spero ............................... 260/397.47 |

OTHER PUBLICATIONS

American Pharmacy, pp. 97–103 – Lyman (1941).

*Primary Examiner*—Leonard Schenkman
*Attorney, Agent, or Firm*—John J. Killinger; Roman Saliwanchik

[57] ABSTRACT

A pharmaceutical vehicle for parenteral administration of medroxyprogesterone acetate is disclosed comprising an aqueous solution of sodium sulfate, quaternary ammonium wetting agent, and a member selected from glycerin, propylene glycol, polyethylene glycol, and polypropylene glycol. The compositions may contain a non-ionic hydrophilic colloid as a preferred adjuvant. Compositions are useful for suspending large amounts, e.g., from 200 to 600 mg./ml. of medroxyprogesterone acetate and maintaining suitable suspendability and syringeability characteristics and are used for the known therapeutic indications for medroxyprogesterone acetate.

4 Claims, No Drawings

MEDROXYPROGESTERONE ACETATE COMPOSITIONS

CROSS REFERENCE TO RELATED APPLICATIONS

This application is a continuation-in-part of application Ser. No. 587,747, filed May 7, 1975 now abandoned, which in turn is a continuation of application Ser. No. 395,667, filed Sept. 10, 1973, now abandoned, which in turn is a continuation of application Ser. No. 296,943, filed July 17, 1972, now abandoned, which in turn is a continuation of application Ser. No. 74,163, filed Sept. 21, 1970, now abandoned, which in turn is a continuation-in-part of application Ser. No. 714,436, filed Mar. 20, 1968, now abandoned, which in turn is a continuation of application Ser. No. 387,230, filed Aug. 3, 1964, now abandoned.

BRIEF SUMMARY OF INVENTION

This invention relates to a pharmaceutical vehicle and compositions utilizing said vehicle and more particularly to an aqueous vehicle suitable for suspending therein large amounts, e.g., from 200 to 600 mg./ml. of medroxyprogesterone acetate, for parenteral administration. The vehicle comprises an aqueous solution of sodium sulfate, a parenterally acceptable quaternary ammonium wetting agent, and a member selected from the group consisting of glycerin, propylene glycol, polyethylene glycol, and polypropylene glycol.

DETAILED DESCRIPTION OF THE INVENTION

Prior to the present invention, the pharmaceutical art, for lack of a suitable vehicle, has had to forego the provision of parenteral dosage forms containing high concentrations, e.g., in excess of 200 ml./ml., of medroxyprogesterone acetate.

The development of a satisfactory parenteral vehicle for suspending medroxyprogesterone acetate has been a heretofore unsolved problem due to the many requirements that the vehicle and composition must satisfy.

Injectable medicinal compositions, taking the form of a suspension are generally sold in two forms: as a prepared ready to use suspension and as a vial of the dry medicinal accompanied by a vial of the aqueous vehicle for extemporaneous mixing to prepare the suspension just prior to administration.

A prepared suspension under modern practice is supplied most frequently in small bottles from which the suspension is withdrawn into a syringe for immediate injection. Such suspensions are also provided in a disposable syringe ready for immediate use. The required physical characteristics of such a suspension can be divided into two categories: suspendability and syringeability.

Primarily, suspendability involves the problems of settling and resuspendability, i.e., caking; and syringeability involves drainage, needle clogging, and freezing of the plunger in the barrel of the syringe. Settling is undesirable for several reasons: it causes uneven dosage due to lack of uniformity in aliquot portions, and formation of a cake which cannot be resuspended and withdrawn. Syringeability involves drainage of the suspension from the vial; freedom from needle clogging and freezing of the plunger in the barrel of the syringe to enable ready administration of the suspension. Additionally parenteral suspensions must be isotonic and non-irritating.

In addition to the above problems which are applicable to all parenteral suspensions, parenteral suspensions containing large amounts of medroxyprogesterone acetate, i.e., in excess of 200 mg./ml., present the additional problem of being in a fluid condition (as opposed to being a paste) and the caking problem following storage is magnified.

It is therefore the object of the present invention to provide an improved vehicle for suspending medroxyprogesterone acetate and compositions comprising the vehicle and medroxyprogesterone acetate not having the aforementioned undesired characteristics.

In the specification and claims all percentages are w/v unless otherwise specified.

The vehicle of the present invention is suitable for suspending medroxyprogesterone acetate in a concentration in excess of 200 mg./ml. comprises an aqueous solution of from about 1.0% to about 2.2% of sodium sulfate, from about 0.2% to about 2% of a parenterally acceptable quaternary ammonium wetting agent and from about 2.7% to about 7% of a member selected from the group consisting of glycerine, propylene glycol, polyethylene glycol, and polypropylene glycol. Additionally, a preferred additional ingredient is up to about 1.5% of a parenterally acceptable non-ionic, hydrophilic colloid.

The compositions of the present invention, i.e. suspensions resulting from combining the vehicle and medroxyprogesterone acetate, comprise from about 200 to about 600 mg./ml. of suspended medroxyprogesterone acetate; water, from about 0.8% to about 1.5% of sodium sulfate; from about 0.1% to about 1.4% of a parenterally acceptable quaternary ammonium wetting agent; and from about 2% to about 5% of a member selected from the group consisting of glycerin, propylene glycol, polyethylene glycol, and polypropylene glycol. Additionally, a preferred additional ingredient is up to about 1.0% of a parenterally acceptable, non-ionic hydrophilic colloid.

The following table shows percentage of the various ingredients in terms of w/v for the vehicle and composition:

| Ingredients | Vehicle (% w/v) | Composition ((% w/v) |
|---|---|---|
| Sodium sulfate | 1.0 to 2.2 | 0.8 to 1.5 |
| Quaternary ammonium wetting agent | 0.2 to 2.0 | 0.1 to 1.4 |
| Member of Group Glycerin Propylene glycol Polyethylene glycol Polypropylene glycol | 2.7 to 7 | 2 to 5 |
| Non-ionic hydrophilic colloid | 0 to 1.5 | 0 to 1.0 |
| Water | q.s. | q.s. |
| Insoluble hydrophobic medroxyprogesterone acetone | none | 20 to 60 |

Quaternary ammonium wetting agents include, for commercial composition, those accepted by the FDA for parenteral administration such as, for example, myristyl gamma picolinium chloride, benzalkonium chloride, cetylpyridium chloride, benzethonium chloride and cetyltrimethylammonium bromide. For compositions utilized for research purposes in laboratory animals, the FDA criteria is not a requisite. The preferred concentration of wetting agent is just that amount which enables a fluid suspension to be prepared and can be up to 2% depending on the type and concentration of drug. Excess amounts of wetting agent will cause caking of the suspension and will give rise to undesirable irritation on injection.

The member selected from the group consisting of glycerin, propylene glycol, polyethylene glycol, i.e., a condensation polymer of ethylene oxide and water, and polypropylene glycol, i.e., a condensation polymer of propylene oxide and water, is present in the preferred concentration of 2% in a composition containing 400 mg./cc. or less of suspended drug. Higher concentrations are used, i.e., up to 5% for higher drug concentrations.

Sodium sulfate is present in a concentration of from 0.8 to 1.5% of the composition. Although sodium sulfate is itself a specifically required ingredient, its concentration within the defined limits is determined with regard to the provision of isotonicity. The weights and percentages given in the specification and claims for sodium sulfate are for the anhydrous compound.

A preferred adjuvant, although not a requirement for purposes of the invention, is a parenterally acceptable non-ionic hydrophilic colloid. Suitable colloids are, for example, polyvinylpyrrolidone, dextran, methylcellulose, hydroxyethylcellulose, and polyvinylalcohol, and are present in a concentration of up to 1.0% for increasing the sedimentation volume.

Water for injection completes the ingredients found in the vehicle.

The medroxyprogesterone acetate agent is reduced to a particle size of a fineness suitable for injection and it is preferred that the drug be micronized, i.e., reduced to a fineness of
99% less than 10 microns and
75% less than 5 microns.

The vehicle of the present invention can be prepared by dissolving the sodium sulfate, quaternary ammonium wetting agent, member selected from the group consisting of glycerin, propylene glycol, polyethylene glycol and polypropylene glycol, and optionally, the non-ionic hydrophilic colloid in water. The solution can be then sterilized by conventional methods, i.e., filtration. Following sterilization, the solution is placed in sterile containers, the usual being 1 to 10 cc. amounts, and sealed.

The compositions are prepared by reducing the particle size of medroxyprogesterone acetate to a size suitable for parenteral administration, preferably of micronized size. For preparation of compositions for commercial sale it is preferred that the drug is incorporated in the vehicle by means of a sterile mill and the composition filled into vials and supplied as a ready to use composition.

The compositions are therapeutically useful for treating the conditions for which medroxyprogesterone acetate are known to be useful, e.g., endometriosis. Because of the higher concentration of medroxyprogesterone acetate per milliliter a smaller volume is injected.

EXAMPLE 1

1000 cc. of the vehicle of the present invention is prepared from the following types and amounts of ingredients by dissolving the ingredients in the water, sterilizing and sealing in suitable vials.

| A | |
|---|---|
| Myristyl gamma picolinium chloride | 4 gm. |
| Polyethylene glycol 4000 | 25 gm. |
| Sodium sulfate | 10 gm. |
| Water for injection q.s. | 1000 cc. |
| B | |
| Myristyl gamma picolinium chloride | 2 gm. |
| Polyethylene glycol 4000 | 25 gm. |
| Sodium sulfate | 16 gm. |
| Water for injection q.s. | 1000 cc. |

In the preceding formulas A and B, one each of the following can be substituted for the myristyl gamma picolinium chloride: benzalkonium chloride, cetylpyridium chloride, benzethonium chloride and cetyltrimethylammonium bromide.

| C | |
|---|---|
| Myristyl gamma picolinium chloride | 3 gm. |
| Polyethylene glycol 4000 | 70 gm. |
| Sodium sulfate | 10 gm. |
| Water for injection q.s. | 1000 cc. |
| D | |
| Myristyl gamma picolinium chloride | 3 gm. |
| Polyethylene glycol 4000 | 27 gm. |
| Sodium sulfate | 10 gm. |
| Water for injection q.s. | 1000 cc. |

In the preceding formulas C and D, one each of the following can be substituted for the polyethylene glycol 4000: glycerin, propylene glycol, polyethylene glycol 1500, polyethylene glycol 400.

| E | |
|---|---|
| Myristyl gamma picolinium chloride | 3 gm. |
| Polyvinylpyrrolidone | 3 gm. |
| Sodium sulfate | 16 gm. |
| Polyethylene glycol 4000 | 60 gm. |
| Water for injection q.s. | 1000 cc. |

The preceding compositions are suitable vehicles for suspending from 200 to 600 mg./ml. of medroxyprogesterone acetate therein.

EXAMPLE 2

1000 Cc. of composition suitable for parenteral administration is prepared from the following types and amounts of ingredients:

| | |
|---|---|
| Medroxyprogesterone acetate micronized | 400 gm. |
| Myristyl gamma picolinium chloride | 2 gm. |
| Polyvinylpyrrolidone | 2 gm. |
| Sodium sulfate | 11.14 gm. |
| Polyethylene glycol 4000 | 20.76 gm. |
| Water for injection q.s. | 1000.0 cc. |

The myristyl gamma picolinium chloride, polyvinylpyrrolidone, sodium sulfate and polyethylene glycol 4000 are dissolved in sufficient water for injection to make about 700 cc. of solution and sterilized by filtration. The medroxyprogesterone acetate is sterilized under ethylene oxide, mixed with the sterile solution previously prepared and passed through a sterile colloid mill. The resulting suspension is filled into sterile vials and sealed.

A dose of 100 mg. (0.25 ml.) is injected I.M. every 2 weeks for the treatment of endometriosis.

EXAMPLE 3

A composition suitable for parenteral administration is prepared from the following types and amounts of ingredients:

| | |
|---|---|
| Medroxyprogesterone acetate micronized | 500 gm. |
| Myristyl gamma picolinium chloride | 2 gm. |
| Polyvinylpyrrolidone | 2 gm. |
| Sodium sulfate | 11.14 gm. |
| Polyethylene glycol 4000 | 20.76 gm. |
| Water for injection q.s. | 1000.0 cc. |

The myristyl gamma picolinium chloride, polyvinylpyrrolidone, sodium sulfate and polyethylene glycol 4000 are dissolved in water for injection to make 700 cc. of solution, the solution sterilized by filtration, 0.7 cc. filled into each vial and the vials capped. The medroxyprogesterone acetate is sterilized under ethylene oxide, 500 mg. filled into each vial and capped. At time of use the sufficient aqueous solution of one vial is added to the contents of the powder vial to make 1 cc. of suspension and the suspension prepared by triturating in a sterile mortar using aseptic technique.

I claim:

1. An aqueous suspension for parenteral administration comprising from about 200 to about 600 mg./ml. of suspended medroxyprogesterone acetate; water; from about 0.8% w/v to about 1.5% w/v of sodium sulfate; from about 0.1% w/v to about 1.4% w/v of a parenterally acceptable quaternary ammonium wetting agent; and from about 2% w/v to about 5% w/v of a member selected from the group consisting of glycerin, propylene glycol, polyethylene glycol and polypropylene glycol.

2. The composition of claim 1 additionally containing a parenterally acceptable non-ionic hydrophilic colloid in a concentration not exceeding 1.5% w/v.

3. The composition of claim 1 wherein the suspended medroxyprogesterone acetate is a fineness of 99% less than 10 microns and 75% less than 5 microns.

4. The composition of claim 3 additionally containing a parenterally acceptable non-ionic hydrophilic colloid in a concentration not exceeding 1.5% w/v.

* * * * *